(12) United States Patent
Dhaon

(10) Patent No.: US 6,262,260 B1
(45) Date of Patent: Jul. 17, 2001

(54) PROCESS FOR THE PREPARATION OF MIDAZOLAM

(75) Inventor: Madhup K. Dhaon, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/533,160

(22) Filed: Mar. 23, 2000

(51) Int. Cl.[7] .................................................. C07D 487/04
(52) U.S. Cl. .............................................................. 540/562
(58) Field of Search ............................................ 540/562

(56) References Cited

U.S. PATENT DOCUMENTS

| | | | |
|---|---|---|---|
| 4,280,957 | 7/1981 | Walser | 260/244.4 |
| 4,377,523 | 3/1983 | Walser | 260/244.4 |
| 4,440,685 | 4/1984 | Walser | 260/245.6 |
| 5,367,084 | * 11/1994 | Verkade et al. | 548/518 |
| 5,693,795 | * 12/1997 | Bender | 540/562 |
| 5,739,329 | * 4/1998 | Sugiyama | 544/224 |

FOREIGN PATENT DOCUMENTS 1549836  8/1979  (GB) .

OTHER PUBLICATIONS

Tilley and Sayigh, J.Org.Chem., 28, 1963, 2076–2079.*

* cited by examiner

*Primary Examiner*—Mark L. Berch
*Assistant Examiner*—Thomas McKenzie
(74) *Attorney, Agent, or Firm*—B. Gregory Donner; Dugal S. Sickert

(57) ABSTRACT

The present invention provides a process for the synthesis of compounds of formula (II)

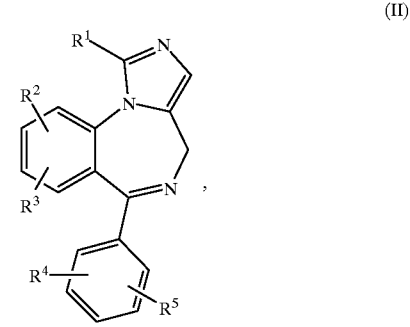

or pharmaceutically acceptable salts thereof.

16 Claims, No Drawings

PROCESS FOR THE PREPARATION OF MIDAZOLAM

TECHNICAL FIELD

The present invention relates to a process for the preparation of 8-chloro-6-(2-fluorophenyl)-1-methyl-4H-imidazo (1,5-a)(1,4)benzodiazepine (Midazolam) from 8-chloro-6-(2-fluorophenyl)-1-methyl-4H-imidazo (1,5-a)(1,4) benzodiazepine-3-carboxylic acid (tricyclic acid).

BACKGROUND OF THE INVENTION

8-Chloro-6-(2-fluorophenyl)-1-methyl-4H-imidazo(1,5-a)(1,4)benzodiazepine (Midazolam), a pre-operative anesthetic, belongs to a class of imidazobenzodiazepine compounds which are useful as anticonvulsants, sedatives, and muscle relaxants. Because of the therapeutic usefulness of these compounds, there is sustained interest in improving their synthesis, particularly the thermal decarboxylation step of the substituted tricyclic acid precursor.

U.S. Pat. No. 4,280,957, U.S. Pat. No. 4,440,685, U.S. Pat. No. 4,377,523, and GB 1,549,836 teach a high temperature decarboxylation of tricyclic acid to provide Midazolam, 8-chloro-6-(2-fluorophenyl)-1-methyl-6H-imidazo (1,5-a)(1,4)benzodiazepine (Isomidazolam) and decomposition by-products resulting from concomitant high temperature dehalogenation and dimerization of the tricyclic acid precursor. This method is impractical for large-scale preparation of Midazolam because of the costly chromatography equipment, plant time, and solvents required.

Attempts at improving the yield of Midazolam have focused on isomerizing purified Isomidazolam to Midazolam. U.S. Pat. No. 4,377,523 and U.S. Pat. No. 4,440,685 teach the isomerism of Isomidazolam to Midazolam by treatment of the former with potassium tert-butoxide in N,N-dimethylformamide (DMF) under kinetically controlled conditions. This method is also impractical for the large-scale syntheses of Midazolam because of the amount of thermal energy required for removal of the DMF.

Commonly owned, pending U.S. application Ser. No. 09/344280, filed Jun. 30, 1999, teaches isomerizing Isomidazolam to Midazolam in a lower-boiling solvent such as methanol, a solvent which is more easily removed than DMF. While this approach is an improvement over the art, there still remains a need in the pharmaceutical manufacturing industry for a lower temperature decarboxylation of imidazobenzodiadepines in general and tricyclic acid, in particular.

SUMMARY OF THE INVENTION

The process of the present invention therefore provides a large-scale decarboxylation of compounds of formula (I) to provide compounds of formula (II) which minimizes isomer formation and provides for non-chromatographic removal of by-products.

In one embodiment of the present invention is provided a process for the synthesis of a compound of formula (II)

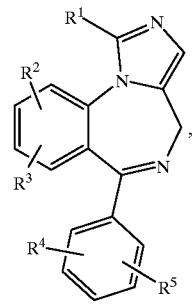

or a pharmaceutically acceptable salt thereof, wherein
  $R^1$ is hydrogen or alkyl; and
  $R^2$, $R^3$, $R^4$, and $R^5$ are independently selected from the group consisting of hydrogen, halo, alkyl, and nitro;
the method comprising:
  (a) decarboxylating a compound of formula (I)

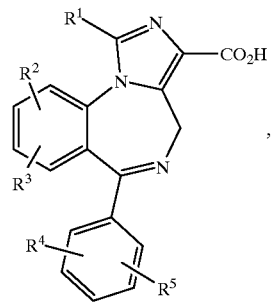

in a solvent of formula (III)

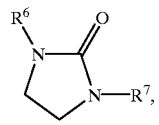

wherein $R^6$ and $R^7$ are alkyl; and
  (b) reacting the product from step (a) with base.

In another embodiment of the present invention is disclosed a method of purifying Midazolam without using column chromatography.

DETAILED DESCRIPTION OF THE INVENTION

Percentages obtained by HPLC analyses were obtained by peak area calculations.

When used throughout this specification, the following terms have the meanings indicated:

The term "activated charcoal," as used herein, represents powdered carbon which is used for the removal of impurities during recrystallization. Activated charcoal of this invention includes Darco®, Norit®, and the like.

The term "alkali metal hydroxide," as used herein, represents $(M)^{+n}(OH)_n^-$, wherein $(M)^+$ is a cation selected from the group consisting of lithium, sodium, potassium, cesium, magnesium, calcium, and barium; and n is one or two.

The term "$C_5$–$C_{10}$ alkane," as used herein, represents a straight or branched chain saturated hydrocarbon of five to ten carbon atoms. Alkanes of this invention include pentane, hexane, heptane, and the like.

The term "alkyl," as used herein, represents a straight or branched chain saturated hydrocarbon radical having from one to six carbon atoms. Alkyl groups of this invention include methyl, ethyl, propyl, tert-butyl, and the like.

The term "base," as used herein, represents a species capable of abstracting a proton in either a polar or a non-polar solvent. Examples of bases include alkali metal hydroxides as defined herein; alkali metal hydrides such as lithium, sodium, or potassium hydride; and nitrogen-containing bases such as lithium diisopropyl amide (LDA), lithium bis(trimethylsilyl)amide, sodium bis(trimethylsilyl) amide, and potassium bis(trimethylsilyl)amide; and the like. It will be apparent to a skilled practiner that individual base and solvent combinations can be preferred for specific reaction conditions depending on such factors as the solubility of reagents, reactivity of reagents with Isomidazolam or the solvent, and preferred temperature ranges.

The term "continuous process," as used herein, represents the conduction of a reaction to provide an intermediate followed by use of the intermediate, without purification, in a subsequent reaction.

The term "halo," as used herein, represents F, Cl, Br, and I.

The term "nitro," as used herein, represents —$NO_2$.

The term "non-polar solvent," as used herein, represents a solvent which is relatively inert to proton activity, i.e., not acting as a proton donor. Examples of non-polar solvents include hydrocarbons such as pentane, hexane, and heptane; aromatic solvents such as benzene, toluene, and nitrobenzene; halogenated hydrocarbons such as dichloromethane, carbon tetrachloride, and 1,2-dichloroethane; and the like.

The term "pharmaceutically acceptable salt," as use herein, represents those salts which are, within the scope of sound medical judgment, suitable for use in contact with the tissues of humans and lower animals without undue toxicity, irritation, allergic response and the like and are commensurate with a reasonable benefit/risk ratio. The salts can be prepared in situ during the final isolation and purification of the compounds of the instant invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to, ammonium, tetramethylammonium, tetraethylammonium, methylamine, dimethylamine, trimethylamine, triethylamine, ethylamine, and the like.

The term "polar solvent," as used herein, represents a solvent which provides protons. Examples of polar solvents include methanol, ethanol, and butanol and solvents polarized by a electron withdrawing groups such as 1,3-dimethyl-2-imidazolidinone, acetonitrile, and the like.

The terms "treated" and "treating," as used herein, refer to contacting, mixing, diluting, or reacting one or more chemical entities by the reasonable and usual manner in which chemicals are combined. Normal concentrations (0.01M to 10M, typically 0.1M to 1M), temperatures (−10° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive reactions) are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Synthetic Methods

The compounds and processes of the present invention will be better understood in connection with the following synthetic scheme which illustrates a method by which the compound of the invention is prepared.

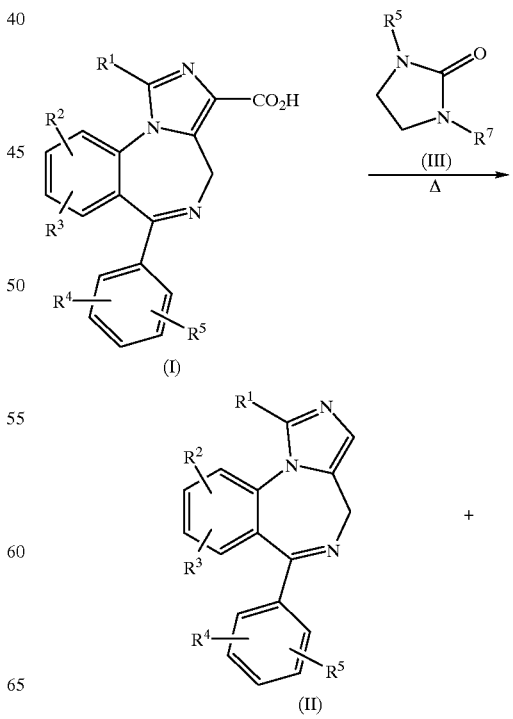

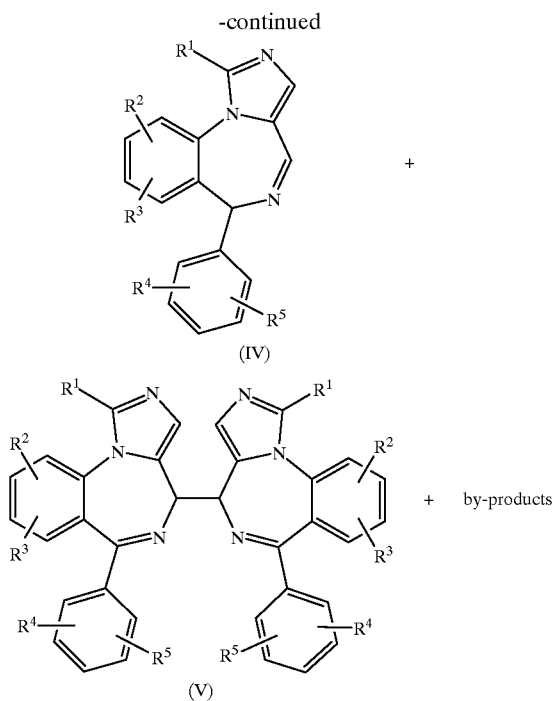

As shown in Scheme 1, compounds of formula (I) can be heated in a solvent of formula (III) at a temperature between about 175° C. and 180° C. until substantially decarboxylates to form compounds of formula (II), compounds of formula (IV), and by-products. In a preferred embodiment, tricyclic acid (formula (I): $R^1$ is methyl; $R^2$ is H; $R^3$ is 8-chloro; $R^4$ is H; and $R^5$ is 2-fluoro) is heated in 1,3-dimethyl-2-imidazolidinone (formula (III): $R^6$ and $R^7$ are methyl) between about 175° C. and 180° C. for about 7 to about 12 hours to provide a 2.5:1 ratio of Midazolam (formula (II): $R^1$ is methyl; $R^2$ is H; $R^3$ is 8-chloro; $R^4$ is H; and $R^5$ is 2-fluoro) to Isomidazolam (formula (IV): $R^1$ is methyl; $R^2$ is H; $R^3$ is 8-chloro; $R^4$ is H; and $R^5$ is 2-fluoro).

After cooling, the reaction solution can be treated with water and ethyl acetate. The aqueous phase can be extracted with ethyl acetate and the combined extracts can be concentrated and dissolved in methanol. For the preferred thermodynamic, basic workup conditions, treatment of the methanol solution with an alkali metal hydroxide, such as sodium hydroxide, and heating the mixture to reflux increased the product ratio of to compounds of formula (II) to compounds of formula (IV). After cooling, the methanol-insoluble compound of formula (V) and its analogs which precipitate can be removed from the reaction mixture by filtration. The filtrate can be concentrated partially, treated with water, refluxed, and cooled to precipitate compounds of formula (II). In a preferred embodiment, the methanol solution described above is treated with sodium hydroxide, heated to reflux, cooled, filtered, partially concentrated, treated with water, heated to reflux, cooled, and filtered to provide a 12:1 ratio of Midazolam to Isomidazolam.

Two recrystallizations from ethyl acetate/heptane or isopropyl acetate/heptane provided compounds of formula (II) of greater than 99.9% purity as determined by HPLC analysis.

EXAMPLE 1

8-chloro-6-(2-fluorophenyl)-1-methyl-4H-imidazo
(1,5-a)(1,4)benzodiazepine

A mixture of 8-chloro-6-(2-fluorophenyl)-1-methyl-4H-imidazo (1,5-a)(1,4)benzodiazepine-3-carboxylic acid (15 g, 40.6 mmol) in 1,3-dimethyl-2-imidazolidinone (145 mL) was heated to 175–180° C. under a nitrogen atmosphere, cooled to room temperature, treated slowly with water (500 mL), and treated with ethyl acetate (200 mL) while stirring. The aqueous layer was extracted with ethyl acetate (200 mL), and the extract was washed with water (200 mL), treated with activated charcoal (2 g), stirred for 4 hours, and filtered through filter aid. The filter was washed with ethyl acetate and the filtrate was concentrated.

The concentrate was dissolved in methanol (150 mL), treated with sodium hydroxide (3.2 g, 80 mmol), heated to reflux for 4 hours, cooled to room temperature, stirred for 16 hours, and filtered. The filtrate was concentrated to a weight of 105 g, heated to reflux, treated with water (165 mL), stirred for 15 minutes, cooled to room temperature, stirred for 10 hours, filtered, washed with water (2×20 mL), and dried. The solid was dissolved in acetonitrile (150 mL), treated with activated charcoal (4 g), stirred for 12 hours, filtered through filter aid, washed with acetonitrile (2×20 mL), and concentrated.

The concentrate was dissolved in ethyl acetate (112 g), treated with activated charcoal (1.3 g), stirred for 12 hours, filtered through filter aid, and washed with ethyl acetate (2×20 mL). The filtrate was concentrated to a weight of 42 g, treated with heptane (40 mL), heated to reflux, and cooled to room temperature. The mixture was allowed to crystallize over 12 hours, filtered, and washed with heptane (40 mL). The solid was dissolved in ethyl acetate (93 g), treated with activated charcoal (1.0 g), treated with heptane (78.0 g) to induce crystallization, filtered, and dried to provide 6.37 g (48% yield, 99.94% HPLC purity) of the desired product.

What is claimed is:

1. A method for preparing a compound of formula (II)

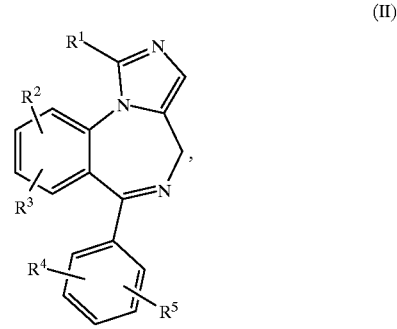

or a pharmaceutically acceptable salt thereof, wherein $R^1$ is hydrogen or alkyl; and $R^2$, $R^3$, $R^4$, and $R^5$ are independently selected from the group consisting of hydrogen, halo, alkyl, and nitro;

the method comprising:

(a) decarboxylating a compound of formula (I) at about °C. to about 180° C.

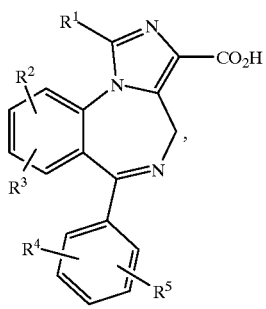

in a solvent of formula (III)

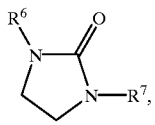

wherein $R^6$ and $R^7$ are independently methyl or ethyl; and (b) reacting the product from step (a) with base.

2. The method of claim 1, wherein the compound of formula (II) is 8-chloro-6-(2-fluorophenyl)-1-methyl-4H-imidazo(1,5-a)(1,4)benzodiazepine.

3. The method of claim 1, wherein the compound of formula (III) is 1,3-dimethyl-2-imidazolidinone.

4. The method of claim 1, wherein the base is an alkali metal hydroxide selected from the group consisting of lithium hydroxide, sodium hydroxide, potassium hydroxide, cesium hydroxide, magnesium hydroxide, calcium hydroxide, and barium hydroxide.

5. The method of claim 4, wherein the alkali metal hydroxide is sodium hydroxide.

6. The method of claim 1, wherein step (b) is conducted at about 20° C. to about 80° C.

7. The method of claim 1, wherein step (a) is conducted for about 7 to about 12 hours.

8. The method of claim 1, wherein step (b) is conducted for about 16 to about 22 hours.

9. The method of claim 1 which is conducted as a continuous process.

10. The method of claim 2, further comprising purifying the compound of formula (II) by recrystallization from a solvent selected from the group consisting of a mixture of heptane and isopropyl acetate and a mixture of heptane and ethyl acetate in the presence of activated charcoal.

11. The method of claim 10, wherein the solvent is a mixture of heptane and ethyl acetate.

12. The method of claim 10, wherein the solvent is a mixture of heptane and isopropyl acetate.

13. The method of claim 10, wherein the compound of formula (II) which is recrystallized is further purified by repeated recrystallization.

14. The method of claim 13, wherein the solvent is a mixture of heptane and ethyl acetate.

15. The method of claim 13, wherein the solvent is a mixture of heptane and isopropyl acetate.

16. The method of claim 13, wherein the solvent is a mixture of heptane and ethyl acetate.

* * * * *